United States Patent
Ryu et al.

(10) Patent No.: US 8,609,034 B2
(45) Date of Patent: Dec. 17, 2013

(54) MICROREACTOR AND LIQUID PHASE CHEMICAL REACTION METHOD USING MICROREACTOR

(75) Inventors: Ilhyong Ryu, Suita (JP); Masaaki Sato, Toyonaka (JP); Takahiro Sagae, Joetsu (JP); Kenichi Hayashi, Joetsu (JP)

(73) Assignees: Nippon Soda Co., Ltd., Tokyo (JP); Osaka Prefecture University Public Corporation, Osaka (JP)

( * ) Notice: Subject to any disclaimer, the term of this patent is extended or adjusted under 35 U.S.C. 154(b) by 470 days.

(21) Appl. No.: 12/734,066

(22) PCT Filed: Oct. 10, 2008

(86) PCT No.: PCT/JP2008/068480
§ 371 (c)(1),
(2), (4) Date: Apr. 8, 2010

(87) PCT Pub. No.: WO2009/048141
PCT Pub. Date: Apr. 16, 2009

(65) Prior Publication Data
US 2010/0210876 A1    Aug. 19, 2010

(30) Foreign Application Priority Data
Oct. 12, 2007    (JP) .................................. 2007-267148

(51) Int. Cl.
*B01J 8/00* (2006.01)
(52) U.S. Cl.
USPC ......................................................... 422/211
(58) Field of Classification Search
USPC ......................................................... 422/211
See application file for complete search history.

(56) References Cited

U.S. PATENT DOCUMENTS

| 3,549,556 | A | * | 12/1970 | Dienes | ........................ 502/250 |
|---|---|---|---|---|---|
| 6,747,178 | B1 | | 6/2004 | Harston et al. | |
| 7,663,008 | B2 | * | 2/2010 | Kobayashi et al. | ........... 585/275 |
| 7,857,874 | B2 | * | 12/2010 | Kihara et al. | ................ 48/127.9 |
| 2007/0161834 | A1 | | 7/2007 | Kobayashi et al. | |

FOREIGN PATENT DOCUMENTS

| JP | A-58-8549 | 1/1983 |
|---|---|---|
| JP | A-58-8550 | 1/1983 |
| JP | A-2001-521816 | 11/2001 |
| JP | A-2004-105864 | 4/2004 |
| JP | A-2006-175361 | 7/2006 |
| JP | A-2006-193483 | 7/2006 |
| JP | A-2007-136345 | 6/2007 |
| JP | A-2007-519601 | 7/2007 |
| WO | WO 2005/073151 A1 | 8/2005 |
| WO | WO 2005/075349 A1 | 8/2005 |

OTHER PUBLICATIONS

Jan. 24, 2012 European Search Report issued in European Patent Application No. 08 83 8325.2.
Wladimir Solodenko et al., "Development of a Continuous-Flow System for Catalysis with Palladium(0) Particles," *European Journal of Organic Chemistry*, Sep. 1, 2004, pp. 3601-3610, vol. 2004, No. 17.
International Search Report issued on Dec. 22, 2008 in International Application No. PCT/JP2008/068480 (with translation).
Kunz et al., "Polymer/Carrier Composites as Materials and Reactors for Organic Synthesis," Journal of Chromatography A, vol. 1006, pp. 241-249, 2003.
Oct. 11, 2012 European Office Action issued in European Application No. 08 838 325.2.
Oct. 8, 2013 Notice of Reasons for Rejection issue in Japanese Application No. 2009-537041 with English-language translation.

* cited by examiner

*Primary Examiner* — Samantha Shterengarts
(74) *Attorney, Agent, or Firm* — Oliff & Berridge, PLC

(57) ABSTRACT

This invention provides a microreactor comprising a microchamber provided with a raw material introduction port and a product discharge port; wherein solid catalysts are aligned in a line in the longitudinal direction of the microchamber to fill the microchamber.

7 Claims, 2 Drawing Sheets

MICROREACTOR AND LIQUID PHASE CHEMICAL REACTION METHOD USING MICROREACTOR

TECHNICAL FIELD

The present invention relates to a microreactor and a liquid phase chemical reaction method using the microreactor. More specifically, the present invention relates to a microreactor capable of conducting a chemical reaction at a high rate, and a method of high-yield liquid phase chemical reaction using the microreactor.

Priority is claimed on Japanese Patent Application No. 2007-267148, filed Oct. 12, 2007, the content of which is incorporated herein by reference.

BACKGROUND ART

Microreactor is a flow type reaction apparatus in which chemical reactions take place in a space (microchannel) with the size of 1 mm or less per one side. Compared to the typical large scale reaction apparatus, in the microreactor, the heat caused by the exothermic reaction can be removed rapidly and the temperature distribution bias can be prevented, because the heat-transfer efficiency is high. Further, expansion to inductrial production is easy since the microreactor can be scaled-up by increasing the number of microchannels in the industrial process.

A microreactor can be manufactured by, for example, forming a groove as a flow channel on a flat substrate by a photolithographic method and covering the flat substrate formed with the groove using a flat plate, the flat plat being provided with a raw material introduction port and a product discharge port (for example, Patent Document 1). Flow channels can be classified into T-shaped, J-shaped, Y-shaped, cyclone-shaped and pillar-shaped flow channels. The microreactor is placed so as to keep the flow channel in a horizontal position, and the chemical reaction takes place in the horizontal flow channel (microchamber).

Meanwhile, the utilization of the microreactor in the gas-phase chemical reaction has a long history and plenty of studies have been made. However, the utilization of microreactor in the liquid phase chemical reaction has a shorter history and many problems remain. For example, in the liquid phase chemical reaction in the microreactor, pressure loss is large and clogging may occur. Furthermore, in a reaction system in which gas is generated by the reaction, since the gas extrudes the contents, an expected reaction time cannot be retained, or since the gas adhere to the surface of the catalyst, contact between the raw material and the catalyst is inhibited, thereby making it impossible to increase the reaction rate.

In order to enlarge the contact area between the catalysts and the reaction raw material in a chemical reaction reactor, a catalyst having a large specific surface area is usually used. For example, a catalyst in which a granular support having a smaller size than the inner diameter of the chemical reaction reactor carries a metal catalyst can be cited as an example. However, when a liquid phase reaction is conducted in a microchamber filled with the granular solid catalysts, channeling (a phenomenon in which an unexpected thick flow channel is formed in a catalyst-filled layer and the raw material fluid only flows into the unexpectedly formed flow channel, and does not flow into other flow channels.) occurs. Therefore, the contact area between the reaction raw material and the catalysts may becomes smaller than the designed value and the reaction rate may become lower.

[Patent Document 1] Japanese Unexamined Patent Application, First Publication No. 2007-136345

DISCLOSURE OF INVENTION

Problems to be Solved by the Invention

The objective of the present invention is to provide a microreactor capable of conducting chemical reaction at a high rate, and a method of high-yield liquid phase chemical reaction using said microreactor.

Means for Solving the Problems

In order to achieve the above object, the inventors of the present invention conducted intensive investigations and discovered that the reaction rate can be improved by conducting a chemical reaction using a microreactor in which solid catalysts are aligned in a line in the longitudinal direction of the microchamber to fill the microchamber. The present invention was completed by conducting further studies on the basis of this finding.

The present invention includes the following aspects:
(1) a microreactor including a microchamber provided with a raw material introduction port and a product discharge port; wherein solid catalysts are aligned in a line in the longitudinal direction of the microchamber to fill the microchamber;
(2) the microreactor according to (1), wherein the solid catalysts are pellet-shaped, tablet-shaped or disc-shaped;
(3) the microreactor according to (1), wherein the solid catalysts are configured in such a manner that a pellet-shaped, tablet-shaped or disc-shaped support carries a catalyst including a transition metal element and/or an acid, or, a transition metal element and/or a base;
(4) a liquid chemical reaction method using the microreactor according to any one of (1) to (3), including introducing a liquid raw material from the raw material introduction port to the microchamber, conducting a chemical reaction in the microchamber to obtain a product, and discharging the product from the product discharge port of the microreactor; and
(5) the liquid chemical reaction method according to (4), wherein the product includes a product in the form of gas.

Effects of the Invention

By using the microreactor of the present invention, a chemical reaction can be conducted at a high rate. Furthermore, a high-yield product can be obtained by conducting a liquid chemical reaction using the microreactor of the present invention. Furthermore, in the microreactor of the present invention, unexpected channeling can be prevented and the contact area between a raw material and solid catalysts can be adjusted as designed value, thereby making it easy to design the microreactor.

The reference symbols shown in the figures are defined as follows:

R1, R2, R3: microchamber
C1, C2: solid catalyst
In: raw material introduction port
Out: product discharge port

BEST MODE FOR CARRYING OUT THE INVENTION

Figure 1:
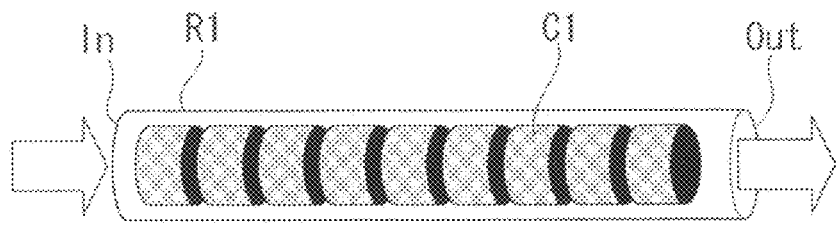
FIG. 1 is a conceptual diagram showing an example of the microreactor of the present invention.
Figure 2:
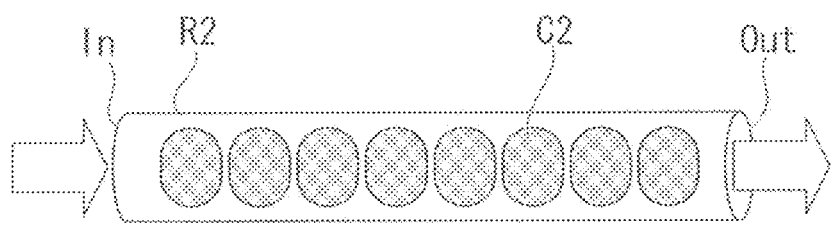
FIG. 2 is a conceptual diagram showing another example of the microreactor of the present invention.
Figure 3:
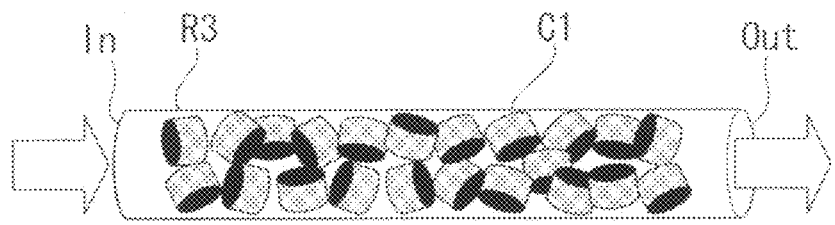
FIG. 3 is a conceptual diagram showing a microreactor in which solid catalysts are randomly filled.

In the embodiment of the present invention, a straight glass tube is used as a microchamber. The straight glass chamber is filled with solid catalysts (C1 or C2), the solid catalysts being aligned in a line in the straight glass chamber as shown in FIG. 1 or FIG. 2. A microchannel is formed between the glass tube and the solid catalysts, and a raw material compound is supplied from one end of the straight glass tube to conduct a reaction, and a desired product discharges from the other end of the straight glass tube. The product obtained from the microreactor of the present invention may include a gas by-product.

The temperature suitable for the microreactor of the present invention is not particularly limited. Although it can be selected according to the chemical reaction, it may be 25 to 250° C., preferably 100 to 200° C. The reaction rate can be easily controlled if the temperature is in the ranges described above.

The microreactor of the present invention includes a microchamber provided with a raw material introduction port and a product discharge port, and the microchamber is filled with solid catalysts that are aligned therein in a line in the longitudinal direction of the microchamber.

In the present invention, a microchamber which is the same as the conventional microreactor can be used. Examples of the microchamber include glass tube, chambers configured in such a manner that a plat plate covers a substrate formed with a groove as a flow channel. A raw material introduction port is provided in at least one end of the microchamber, and a product discharge port is provided in the other end of the microchamber. The raw material is supplied to the raw material introduction port and discharged from the raw material discharge port.

The layout of the flow channel of the microchamber can be selected according to the number and species of the raw materials. For example, it is allowed that a Y-shaped or T-shaped flow channel is prepared to introduce two kinds of raw materials from the two introduction ports, and the two kinds of raw materials are mixed in the junction of the flow channels to conduct a reaction. Further, it is also allowed that the raw material is introduced from one of the introduction ports and homogeneous catalysts are introduced from the other introduction ports, and the raw material and the catalysts are mixed in the junction of the flow channels to conduct a reaction. The raw material to be introduced may be a material in the form of liquid or gas, although a material in the form of liquid is preferred since it derives advantages from the features of the microreactor.

The inner volume of the microchamber is not particularly limited, although it is preferably about 10 μm to 5000 μm per side. Further, the microchannel formed after filling the solid catalysts therein is preferably about 1 μm to 1000 μm per side. If one side of the microchannel is too small, it becomes difficult to supply the raw material due to the increasing of the pressure loss. On the other hand, if one side of the microchannel is too large, the advantages obtaining from the features of the microreactor decreases since the heat-exchange efficiency decreases and a temperature distribution bias occurs. The length of the flow channel of the microchamber is not particularly limited, although it is preferably 10 to 300 cm.

The microreactor of the present invention is configured in such a manner that solid catalysts are filled in the microchamber.

As for the solid catalyst, a catalyst formed by solidifying a powder of a catalyst may be used, or a supported catalyst in which a catalyst is supported by a support may be used.

The catalysts can be selected according the species of the chemical reaction. The representative examples of the catalysts include a catalyst including a transition metal element and/or an acid, or, a transition metal and/or a base.

Examples of the transition metal element include tantalum, molybdenum, tungsten, ruthenium, osmium, palladium, nickel, iron, cobalt, chromium, rhodium, iridium, platinum, gold, silver, copper, titanium and niobium.

Examples of the catalysts including acid or base include acid catalyst such as silica-alumina composite oxide, zeolite, a $Nb_2O_5$—$MoO_3$ composite oxide, $Nb_2O_5 \cdot nH_2O$, a proton type strong acidic beads-shaped fluorine-containing resin or titania-silica composite oxide; a base catalyst such as magnesium alkoxide, magnesium oxide, calcium oxide or sodium alkoxide.

Examples of the support include carbon, silica, silica-alumina, alumina, celite, calcium carbonate, zinc carbonate, barium carbonate, strontium carbonate and the like. Further, the shape of the support is not limited and examples of the shape of the support include a pellet-shape, a tablet-shape, a disc-shape, a globular shape, a ring-shape, a mesh-shape, a honeycomb-shape, an indefinite shape, and the like. Among these, pellet-shape, tablet-shape and disc-shape are preferable. The size of the solid catalyst can be selected according to the inner diameter of the microchamber so that the solid catalysts are aligned in the microchamber in a line in a longitudinal direction. If the size of the solid catalyst is too small compared to the inner diameter of the microchamber, the solid catalysts may be aligned in two lines. Therefore, the size of the solid catalyst is preferably 70% or more of the inner diameter of the microchamber. In addition, the word "be aligned in a line" does not only mean that the solid catalysts are aligned only in a straight line, but also means that the solid catalysts are aligned in a curved line, such as a zigzag or the like.

The solid catalysts are aligned in the microchamber in a line in a longitudinal direction of the microchamber to fill the microchamber. Examples of the solid catalyst include, as shown in FIG. 1, a solid catalyst made by aligning pellet-shaped (column-shaped) solid catalysts (C1) in a line in a longitudinal direction of the microchamber (R1) to fill the microchamber, the direction being the same as the direction of the height of the column; as shown in FIG. 2, a solid catalyst made by aligning globular shaped catalysts (C2) in a line in a longitudinal direction of the microchamber (C2) to fill the microchamber. By aligning the catalysts in such a manner as described above, the raw material is able to mainly pass through the space (microchannel) between the solid catalysts and the inner wall of the microchamber. As a result, unexpected channeling can be prevented and it becomes easy to design the microreactor since the contact area between the raw material and the solid catalysts can be adjusted as the designed value. If the microchannel is straight along the glass tube, even in the case where a gas is generated by the liquid phase chemical reaction, the gas is easily extruded from the product discharge port. Furthermore, by supporting and fixing the solid catalysts on the inner wall of the microchamber, the reaction efficiency becomes higher since the raw material can contact both the catalysts aligned in a line and the catalysts supported on the inner wall.

The used amount of the catalyst is not particularly limited. Although it can be selected according to the supplied amount of the raw material (reaction substance), it is generally 0.01 to 100 mol % with respect to the reaction substance, preferably 0.1 to 50 mol %, and more preferably 0.1 to 10 mol %.

The microreactor is preferably provided with an apparatus supplying a raw material to the microchamber, for example, a pump or the like. The raw material-supplying apparatus is preferably an apparatus that does not cause a pulse when supplying the raw material. In order to deliver the solution steadily, an Electro Osmotic Flow can be used.

In the present invention, the raw material may be supplied to the microreactor directly, or may be supplied to the microreactor after dissolving it in a solvent such as water, methanol, isopropylether, benzene, hexane.

The supplied-amount per hour (flow rate) of the raw material can be selected according to the amount of catalysts, although it is generally 0.1 to 500 ml/h, preferably 0.5 to 50 ml/h, and more preferably 1.0 to 5 ml/h.

Further, the supplied-amount per hour of the raw material is preferably 1 to 1000 mmol/h, and more preferably 10 to 160 mmol/h when measured by the contact amount per 1 mmol of catalyst.

EXAMPLES

Next, the present invention will be described in more detail using the examples, although the scope of the present invention is in no way limited by these examples.

Figure 4:
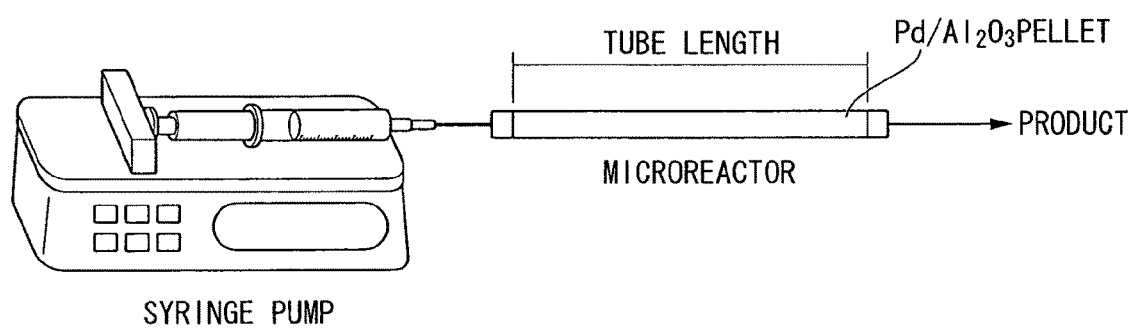
FIG. 4 is a conceptual diagram showing an example of the microreactor provided with a raw material feeding apparatus.

The reaction was conducted using the apparatus shown in FIG. 4. A microreactor (described in FIG. 4 as MICROREACTOR) configured in such a manner that a stainless steel tube of 4 mm in diameter was filled with catalyst-supported pellets that are aligned therein in a line in a longitudinal direction, the catalyst being 3 mm in diameter and 3.5 mm in length, was used. As for the pellet, a pellet in which 0.5% by weight of palladium is supported on the surface of an alumina (manufactured by N.E. CHEMCAT CORPORATION) was used.

Example 1

A 150 mm-long tube filled with 2150 mg of pellets (43 pellets, each weighing 50 mg were used, the supported palladium being 0.85 mol % with respect to the reactive substrate) was used as a microreactor. A solution obtained by dissolving 4.1 g (20 mmol) of iodobenzen and 2.0 g (20 mmol) of phenylacetylene in 3 ml of N,N-dimethylacetamide was filled in a gas tight syringe, and the reaction was conducted at a temperature of 100° C. The flow rate was set to 1.0 ml/h and the retention time was set to 30 min. The resulting reaction solution was analyzed by high performance liquid chromatography, and it was confirmed that the product was obtained quantitatively.

Example 2

A 150 mm-long tube filled with 2150 mg of pellets (43 pellets, each weighing 50 mg were used, the supported palladium being 0.85 mol % with respect to the reactive substrate) was used as a microreactor. A solution obtained by dissolving 4.1 g (20 mmol) of iodobenzen, 2.1 g (24 mmol) of acrylic acid methyl ester and 3.4 g (34 mmol) of triethylamine in 3 ml of N-methylpyrolidone was filled in a gas tight syringe, and the reaction was conducted at a temperature of 120° C. The flow rate and retention time was set as shown in Table 1. The resulting reaction solution was analyzed by high performance liquid chromatography, and the results are shown as Table 1.

TABLE 1

| | Flow rate (ml/h) | Retention time (min) | Yield (%) |
|---|---|---|---|
| 2-1 | 0.1 | 300 | 100 |
| 2-2 | 0.5 | 60 | 100 |
| 2-3 | 1.0 | 30 | 100 |
| 2-4 | 1.25 | 24 | 100 |
| 2-5 | 1.5 | 20 | 100 |
| 2-6 | 2.0 | 15 | 100 |
| 2-7 | 3.0 | 10 | 100 |

Example 3

A 250 mm-long tube filled with 3600 mg of pellets (72 pellets, each weighing 50 mg were used, the supported palladium being 0.85 mol % with respect to the reactive substrate) was used as a microreactor. A mixture obtained by mixing 2.1 g (20 mmol) of benzaldehyde and 1.2 g (20 mmol) of nitromethane was filled in a gas tight syringe, and the reaction was conducted at a temperature of 60° C. The flow rate was set to 2.2 ml/h and the retention time was set to 1 hour. After analyzing the resulting product by $^1$H-NMR, it was confirmed that the inversion rate was 18%, and the objective substance of 2-nitro-1-phenyl-ethanol was approximately obtained quantitatively.

Example 4

A 250 mm-long tube filled with 3600 mg of pellets (72 pellets, each weighing 50 mg were used, the supported palladium being 3.38 mol % with respect to the reactive substrate) was used as a microreactor. A mixture obtained by mixing 528 mg (5 mmol) of phenylacetylene and 5 ml (12 mol equivalent with respect to phenylacetylene) of allylbromide was filled in a gas tight syringe, and the reaction was conducted at room temperature. The flow rate was set to 1.1 ml/h and the retention time was set to2 hours. After analyzing the resulting reaction solution by a gas chromatography, it was confirmed that the inversion rate was 43%, and the desired products of 1-bromo-1-phenyl-1,3-buthadien and 1-bromo-2-phenyl-1-butene were obtained at a yield of approximately 90%.

Comparative Example 1

A 100 mm-long tube filled with 0.5% by weight of palladium-supported alumina powder (the supported Pd being equivalent to 0.85mol % with respect to the reactive substrate) was used as a microreactor. As in Example 1, a solution obtained by dissolving 4.1g (20 mmol) of iodobenzen and 2.0 g (20 mmol) of phenylacetylene in 3 ml of N,N-dimethylacetamide was filled in a gas tight syringe to conduct a reaction at a temperature of 100 ° C. The flow rate was set to 0.1 ml/h and the retention time was set to 40 min. After analyzing the resulting reaction solution by a high performance liquid chromatography, it was confirmed that the product was obtained quantitatively. However, it was impossible to raise the flow rate further since the pressure loss increases when the flow rate is raised to more than 0.1 ml/h.

According to the Examples 1 to 4 and Comparative Example 1, it is apparent that when using a microreactor in which solid catalysts are aligned in a line (Examples 1 to 4), the pressure loss can be reduced and the flow rate can be raised compared to when a microreactor in which solid catalysts are randomly filled was used (Comparative Example 1), thereby enabling it to conduct a chemical reaction at a high efficiency.

INDUSTRIAL APPLICABILITY

By using the microreactor of the present invention, the pressure loss can be reduced and the flow rate can be raised, thereby making it possible to conduct a chemical reaction at a high efficiency. Furthermore, a high-yield product can be obtained by conducting a chemical reaction using the microreactor. Furthermore, in the microreactor of the present invention, unexpected channeling can be prevented and the contact area between a raw material and solid catalysts can be adjusted as designed value, thereby making it easy to design the microreactor. Therefore, the present invention is industrially useful.

The invention claimed is:
1. A microreactor, comprising:
a microchamber provided with a raw material introduction port and a product discharge port; wherein
solid catalysts are aligned in a line in a longitudinal direction of the microchamber to fill the microchamber, and
the solid catalysts are pellet-shaped, tablet-shaped, or disc-shaped.
2. The microreactor according to claim 1, wherein the solid catalysts are configured in such a manner that a pellet-shaped, tablet shaped or disc shaped support carries a catalyst including a transition metal element and/or an acid, or a transition metal element and/or a base.
3. A liquid chemical reaction method using the microreactor according to claim 1, comprising:
introducing a liquid raw material from the raw material introduction port to the microchamber,
conducting a chemical reaction in the microchamber to obtain a product, and
discharging the product from the product discharge port of the microreactor.
4. The liquid chemical reaction method according to claim 3, wherein the product includes a product in the form of gas.
5. A liquid chemical reaction method using the microreactor according to claim 2, comprising:
introducing a liquid raw material from the raw material introduction port to the microchamber,
conducting a chemical reaction in the microchamber to obtain a product, and
discharging the product from the product discharge port of the microreactor.
6. The liquid chemical reaction method according to claim 5, wherein the product includes a product in the form of gas.
7. A microreactor, comprising:
a microchamber provided with a raw material introduction port and a product discharge port; and
pellet-shaped, tablet-shaped, or disc-shaped solid catalysts aligned one by one in a row in a longitudinal direction of the microchamber, the row being a straight line or a curved line.

* * * * *